(12) United States Patent
Maki

(10) Patent No.: US 6,607,526 B1
(45) Date of Patent: Aug. 19, 2003

(54) LASER IRRADIATION APPARATUS

(75) Inventor: Shin Maki, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 361 days.

(21) Appl. No.: 09/695,314

(22) Filed: Oct. 25, 2000

(30) Foreign Application Priority Data

Oct. 27, 1999 (JP) ............................................. 11-305078

(51) Int. Cl.[7] ............................................. A61B 18/18
(52) U.S. Cl. ........................... 606/16; 606/13; 606/14; 606/17; 600/101; 607/92; 607/93
(58) Field of Search ................................ 606/7, 10–19, 606/22, 23, 41, 46; 607/88, 89, 92, 93; 600/101, 103, 104, 106–108, 114, 117, 118; 604/20, 21

(56) References Cited

U.S. PATENT DOCUMENTS

| 4,932,956 A | 6/1990 | Reddy et al. |
| 4,932,958 A | 6/1990 | Reddy et al. |
| 5,207,672 A | 5/1993 | Roth et al. |
| 5,292,320 A | 3/1994 | Brown et al. |
| 5,496,308 A | 3/1996 | Brown et al. |
| 6,530,921 B1 * | 3/2003 | Maki .......................... 606/15 |

FOREIGN PATENT DOCUMENTS

| EP | 0 673 627 | 9/1995 |
| WO | 92/04934 | 4/1992 |
| WO | 93/04727 | 3/1993 |

* cited by examiner

*Primary Examiner*—Linda C. M. Dvorak
*Assistant Examiner*—A. Farah
(74) *Attorney, Agent, or Firm*—Burns, Doane, Swecker & Mathis, LLP

(57) ABSTRACT

A laser irradiation apparatus comprising: a long and slender main body 101; an optical fiber 107, which is placed inside the main body 101 and which is equipped with a proximal end through which a laser ray is introduced and an emitting part from which the laser ray is emitted sideways or diagonally; and a reflecting member 151, which is affixed inside said main body 101 and reflects laser ray emitted from the optical fiber 107. The emitting part of the optical fiber 107 is capable of making a reciprocating motion in the lengthwise direction inside the main body 101 within the specified range. The reflecting member 151 has a reflecting surface 152 that changes its reflecting angle as the emitting part of the optical fiber 107 moves along its reciprocating movement range.

11 Claims, 11 Drawing Sheets

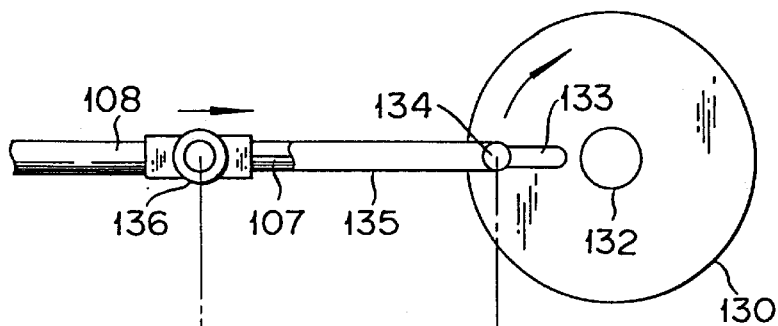
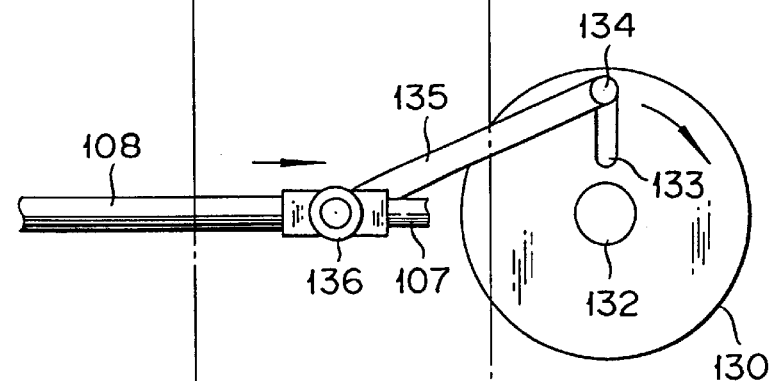
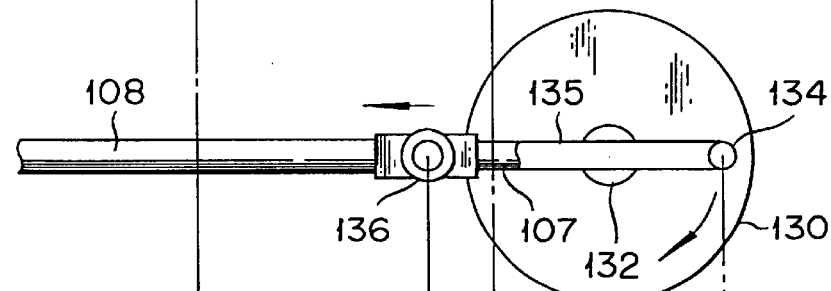
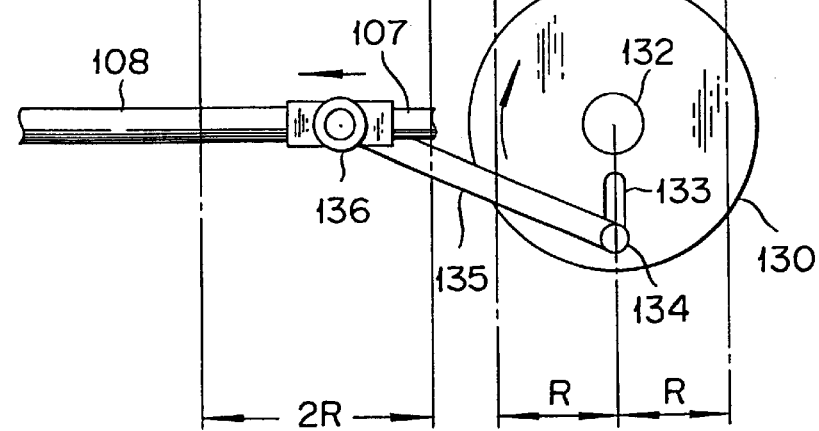

LASER IRRADIATION APPARATUS

BACKGROUND OF THE INVENTION

1. Field of the Invention

The invention relates to a laser irradiation apparatus, more specifically, to a medical laser irradiation apparatus for the treatment of tumors such as cancer or diseases such as benign prostatic hyperplasia by irradiating vital tissues with laser rays by means of inserting the apparatus into vital lumens such as blood vessels, urethras, and abdominal cavities, or puncturing internal organs with it leaving the long main body of the apparatus.

2. Description of the Related Art

A technique of treating lesions by means of laser irradiation apparatuses has been known, where the long and slender main body of a laser irradiation apparatus is inserted into a body cavity or a lumen formed by small discission and lesion tissues are irradiated with energy in order to diminish or clear the lesion tissues through alteration, sphacelation, coagulation, cauterization and evaporation.

The technique is generally to irradiate a lesion existing on the surface layer of a vital tissue or its vicinity directly. However, in order to apply this technique to a deep lesion, heating the lesion to a sufficient temperature, it is necessary to irradiate it with a laser ray of a relatively high power. As a result, there is a possibility damaging normal tissues adjacent to the lesion, such as the surface layer.

International Publication No. WO93/04727 disclosed a technique for coagulating and diminishing a tumor or a part of prostate by means of laser irradiation. The technique includes a method of using a cooling liquid led into a balloon in order to heat mainly the targeted internal tumor or the prostate minimizing the heating the surface of the urethra that is adjacent to the balloon. However, since the laser ray is irradiated from a fixed laser irradiator in this case, the technique has a drawback that it is necessary to use a low-power laser ray so as not to heat the surface of the urethra, thus resulting in a long irradiation time.

Unexamined Publication No. JP-A-6-154239 disclosed a laser irradiation apparatus to be inserted into the urethra for treating benign prostatic hyperplasia with laser rays. In this technique, multiple irradiation units placed at different positions radiate laser rays. The irradiated laser rays are converged on a target site in a deep legion to generate a sufficient heat for heating and diminishing the legion tissue. Consequently, the temperature in the vicinity of the target site becomes higher than other parts where the laser rays do not overlap. However, since the light paths of the laser rays are fixed, a certain region is created in the vicinity of the surface layer of the urethra where the laser rays do not overlap but the temperature is slightly higher. This phenomenon disadvantageously affects the protection of the surface layer of the urethra. Therefore, it is not completely satisfactory from the standpoint of treating only a deep lesion while preventing damages on the surface layer.

SUMMARY OF THE INVENTION

The object of the invention is to provide an apparatus that effectively irradiates a target site with laser rays, particularly a target site hidden deep inside a vital tissue, while easily and securely preventing damages to normal tissues, particularly, normal surface tissues that are in contact with the laser irradiation apparatus.

The specific object of the invention is to provide a laser irradiation apparatus comprising: a long and slender main body; a light conducting member, which is placed inside said main body and which is equipped with a proximal end through which the laser rays are introduced and an emitting part from which the laser rays are irradiated sideways or diagonally, wherein said emitting part of said light conducting member can move reciprocally in the axial direction within a certain range; and a reflecting member, which is affixed to the inside of said main body to reflect the laser rays irradiated from said light conducting member, wherein said reflecting member having a reflecting surface that changes its reflecting angle as said emitting part moves along its reciprocating movement range.

The laser irradiation apparatus of the present invention makes it possible to converge the laser rays emitted from the continuously moving emitting part on the target site or its vicinity. This enables areas other than the target site to be maintained at relatively low temperatures. Thus, the damages to areas other than the target site will be prevented or kept minimum, so that it can provided a high treatment effect. It is particularly effective in a case where the target site is hidden deep inside the vital tissue as the damages to the surface layer can be kept minimum.

The objects, features, and characteristics of this invention other than those set forth above will become apparent from the description given herein below with reference to preferred embodiments illustrated in the accompanying drawings.

BRIEF DESCRIPTION OF THE DRAWINGS

FIG. 8A–FIG. 8D are plan views to describe the reciprocating motion of the optical fiber of the laser irradiation apparatus;

DETAILED DESCRIPTION OF THE PREFERRED EMBODIMENT

Figure 1:
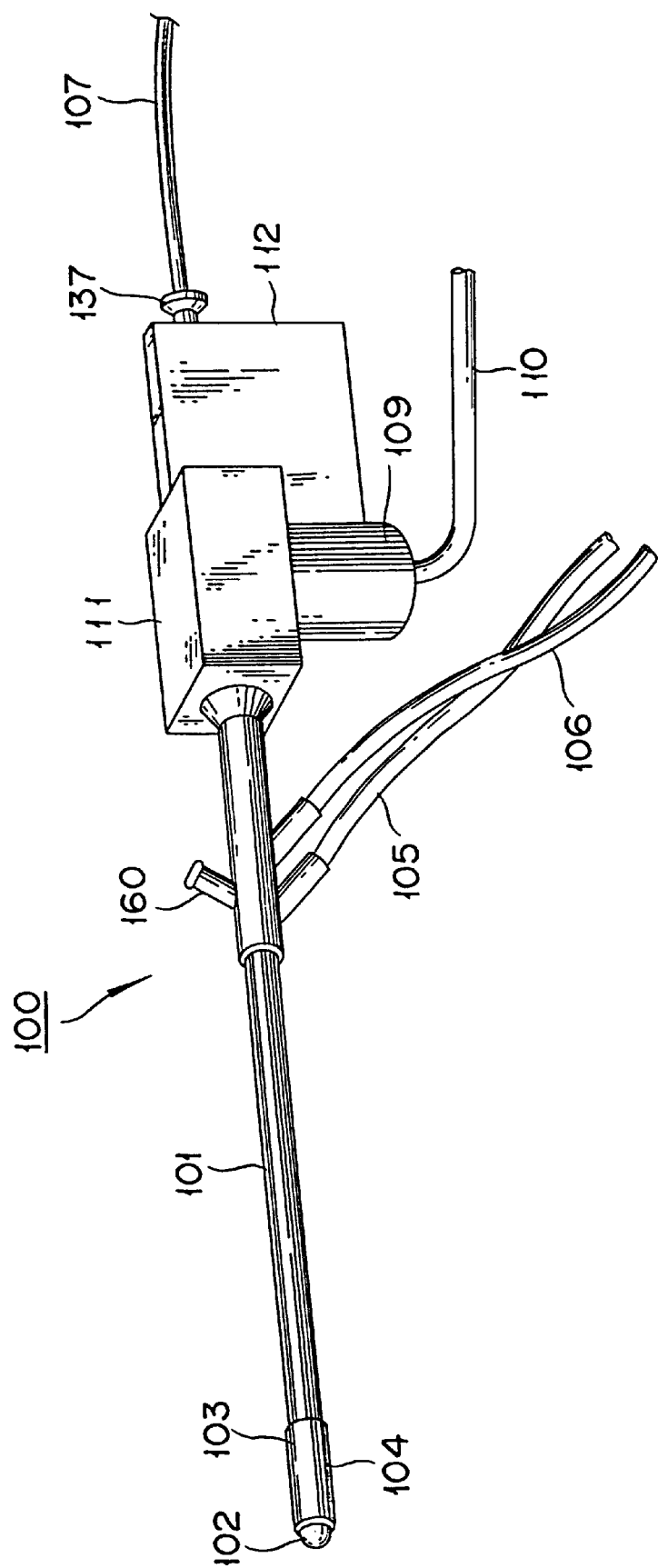
FIG. 1 is an outline perspective drawing of a laser irradiation apparatus in accordance with the preferred embodiment of the invention.
Figure 2:
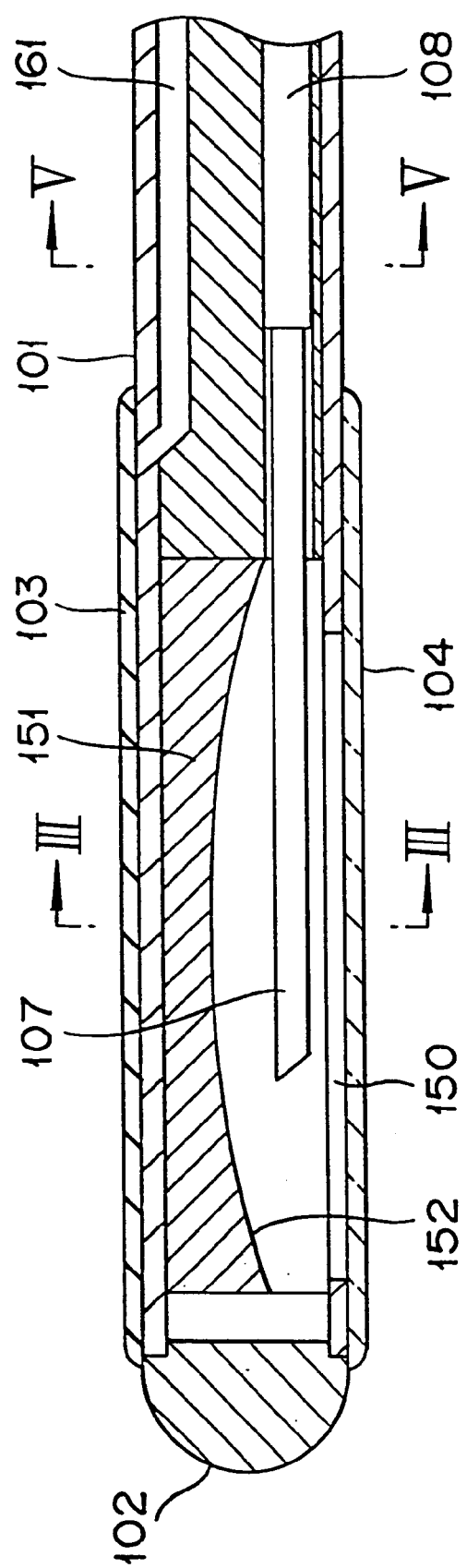
FIG. 2 is a drawing to describe the structure of the distal end of the main body of the laser irradiation apparatus according to the first embodiment.

The embodiments of this invention will be described below with reference to the accompanying drawings.

The laser irradiation apparatus 100 according to the first embodiment of this invention shown in FIG. 1, FIG. 2, FIG. 3A and FIG. 3B is of a side emitting type and is used for the treatment of ailing tissues such as benign prostatic hyperplasia.

The apparatus 100 has a long and slender tube-like main body 101, a drive unit 109, a cam box 111, and a buffer unit 112, and is connected to a laser ray generating unit, a cooling liquid circulating unit and a power unit (not shown).

The main body 101 has a tube-like shape and is made of a hard material such as metal, e.g., stainless steel, or other materials. The distal end of the main body 101 is provided with an end cap 102 for a sealing purpose and a window 150, which is an opening for allowing laser rays to pass through.

The inside of the main body 101 is provided with an optical fiber 107, which is the light conducting member, to be able to slide freely. Laser rays are injected through the proximal end of the optical fiber 107 into it by the laser generating unit, guided through the optical fiber 107, and are emitted sideways or tangentially from the distal end of the optical fiber.

Figure 4:
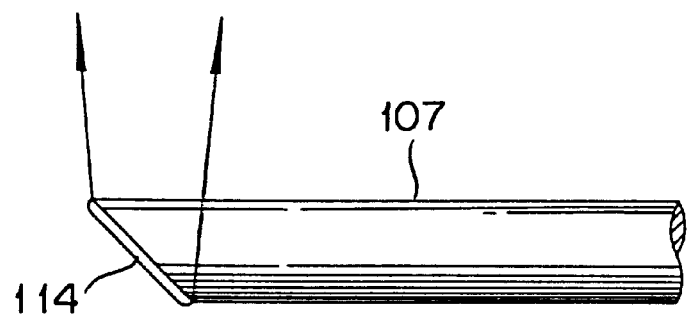
FIG. 4 is a side view of the distal end of an optical fiber to describe the structure of its distal end.

As shown in FIG. 4, the distal end of the optical fiber 107 has a flat surface cut in an angle of approximately 35–50 degrees, or preferably 45 degrees, relative to the axis of the optical fiber 107. The flat surface is coated with a reflective film 114. A metal film made of a metal such as gold formed by gluing, vapor-depositing, or plating, or a multi-layered film formed by vapor-depositing reciprocally a dielectric material of a high reflectivity and a dielectric material of a low reflectivity is used as the reflective film 114. $Al_2O_3$, $ZrO_2$, $TiO_2$, $CeO_2$, etc., are used as the dielectric materials of high reflectivity, and $MgF_2$, $SiO_2$, etc., are used as the low reflectivity dielectric. The thickness of the reflective film 114 is preferably 0.2–1.0 $\mu$m. The laser rays that have been guided through the optical fiber 107 are reflected at the reflective film 114 and are emitted in the side direction (in the direction of the arrow of FIG. 4) of the fiber.

The optical fiber 107 reciprocates driven by the drive unit 109. The drive unit 109 is preferably equipped with an electrical device such as a motor. Electric power is supplied to the drive unit 109 through a cable 110. The rotation of the motor is converted into a reciprocating motion by means of a cam and others. The cam is stored in the cam box 111.

The distal end of the main body 101 is attached with a reflecting member 151, which reflects laser rays. The reflecting member 151 extends in the axial direction of the main body 101 and has a reflecting surface 152 consisting of a parabolically curved surface.

The laser ray irradiated from the optical fiber 107 while the optical fiber 107 is performing the reciprocating motion is reflected by the reflecting surface 152 of the reflecting member 151. The emitting position of the laser ray emitted from the optical fiber 107 continuously changes because of the motion of the distal end of the optical fiber 107. The emitting angle of the laser ray from the optical fiber 107 is constant, and the position where the laser ray lands on the reflecting surface 152 changes continuously. However, the reflecting surface 152 has a continuous strip-like surface with a parabolic curve to cause the parallel rays into one spot. At a result of that, the laser rays reflected by the reflecting surface 152 are converged on the spot existing in the outside of the window 150. Similar to the distal end of the optical fiber, a metal film made of a metal such as gold formed by gluing, vapor-depositing, or plating, or a multi-layered film formed by vapor-depositing reciprocally a dielectric material of a high reflectivity and a dielectric material of a low reflectivity is preferably used as the reflective surface 152. $Al_2O_3$, $ZrO_2$, $TiO_2$, $CeO_2$, etc., are used as the dielectric materials of high reflectivity, and $MgF_2$, $SiO_2$, etc., are used as the low reflectivity dielectric.

The reflective member 151 has a pair of plate-like parts 153 on both sides. The plate-like parts 153 can be formed integral with the reflecting member 151, or can be made separately and affixed to it. The optical fiber 107 reciprocates in the space defined by the inner surfaces of the pair of plate-like parts 153 of the reflecting member 151. While it is preferable to design in such a way that the inner surfaces of the plate-like parts 153 of the reflecting member 151 surrounding the optical fiber 107 do not to fall in the laser path, it is also preferable, as a preventive measure, to have them coated with reflecting films the same way as the reflecting surface 152 in order to reflect the laser rays effectively even if a portion of them fall in the laser path.

Figure 3A:
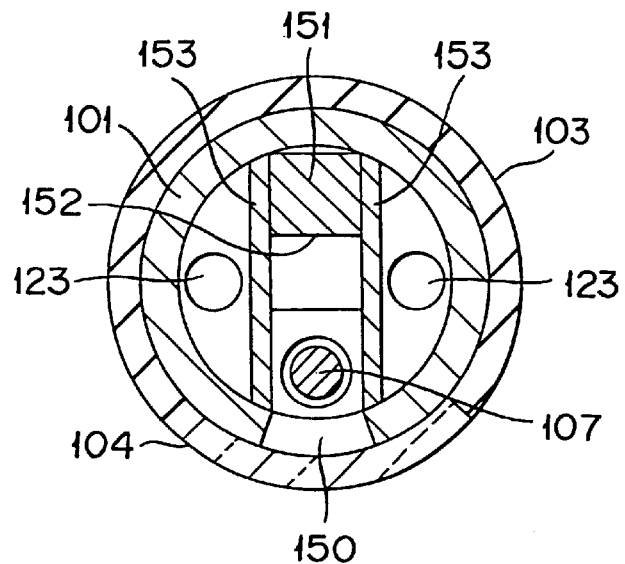
FIG. 3A is a cross sectional view taken along the line III—III of FIG. 2.
Figure 3B:
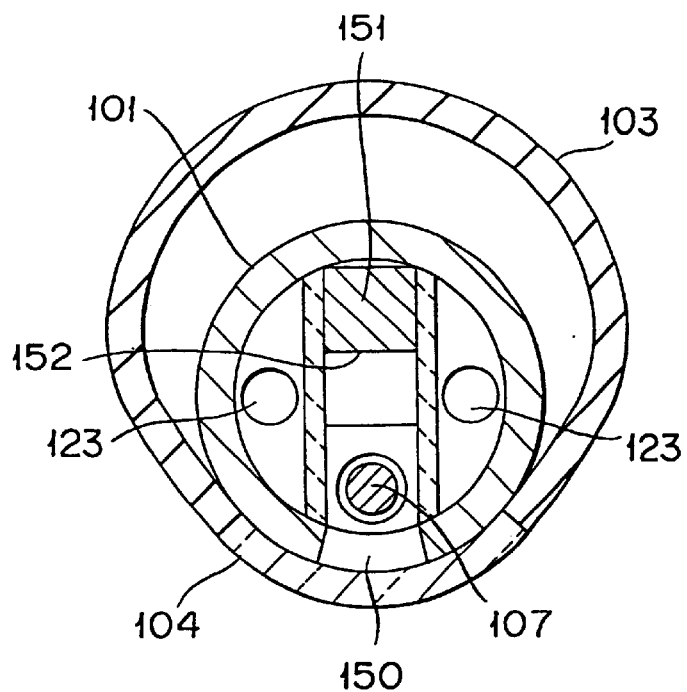
FIG. 3B is the same cross sectional view as that of FIG. 3A except that it shows the condition when the balloon is inflated.

A balloon 103 is placed on the surface of the distal end of the main body 101 covering the surface except the areas of the window 150 and the cover 104. The balloon 103 is made of a plastic film and is arranged in such a way as to be able to expand in the areas except the window 150, through which laser rays are transmitted. The balloon 103 expands as a liquid is injected from the balloon inflating port 160 and plays a role of pressing the window 150 side to the surface of the vital tissue. The balloon inflating port 160 communicates with the balloon expansion lumen 161. The liquid injected through the balloon inflating port 160 is sent into the balloon 103 via the inflating lumen 161. The balloon does not exist in the vicinity surrounding the window of the housing 102 as mentioned before. The light transmitting cover 104 is glued to the surface of the distal end of the main body 101 to cover the area of the window 150. FIG. 3B is the same cross sectional view as that of FIG. 3A except that it shows the condition when the balloon 103 is inflated.

The cooling liquid is induced into the main body 101 through a cooling liquid inducing tube 105 and discharged from the main body 101 through a cooling liquid discharging tube 106. The cooling liquid is circulated through the main body 101 to cool the surface of the vital tissue, the laser-emitting end and the reflecting part of the housing 102. The cooling liquid is circulated by means of a cooling liquid circulating pump unit (not shown).

Figure 5:
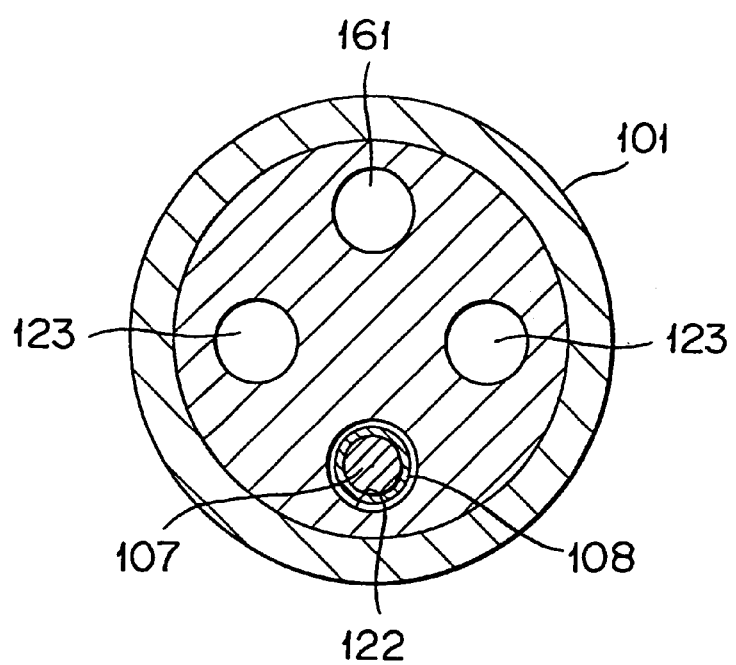
FIG. 5 is a cross sectional view taken along the line V—V of FIG. 2.

In FIG. 5, the optical fiber 107 covered by the protective pipe 108 is inserted into a lumen 122 in such a way that the former can reciprocate freely. The protective pipe 108 extends to the all the way to the cam box 111 covering the entire length of the optical fiber except its distal end. The lumen 122 is formed parallel to the axis of the main body 101 communicating with the tube 105 of FIG. 1 and the cooling liquid flows through the lumen 122. An O-ring (not shown) is provided at the proximal end of the lumen 122 to seal between the protective pipe 108 and the lumen 122.

The cooling liquid induced into the lumen 122 is discharged via an exit lumen 123. The lumen 123 communicates with the discharging tube 106 shown in FIG. 1. It is preferable to have a check valve (not shown) at the distal end of the lumen 123 to prevent the reverse flow of the cooling liquid. The lumen 123 communicates with a space outside of the reflecting member 151 in the main body 101 as shown in FIG. 3.

The cooling liquid induced by the tube 105 flows into the internal space of the main body 101 at the distal end through the lumen 122, changes its direction of flow at the distal end of the main body 101, flows into the lumen 123 passing the outside of the reflecting member 151, and exits via the tube 106.

Figure 6:
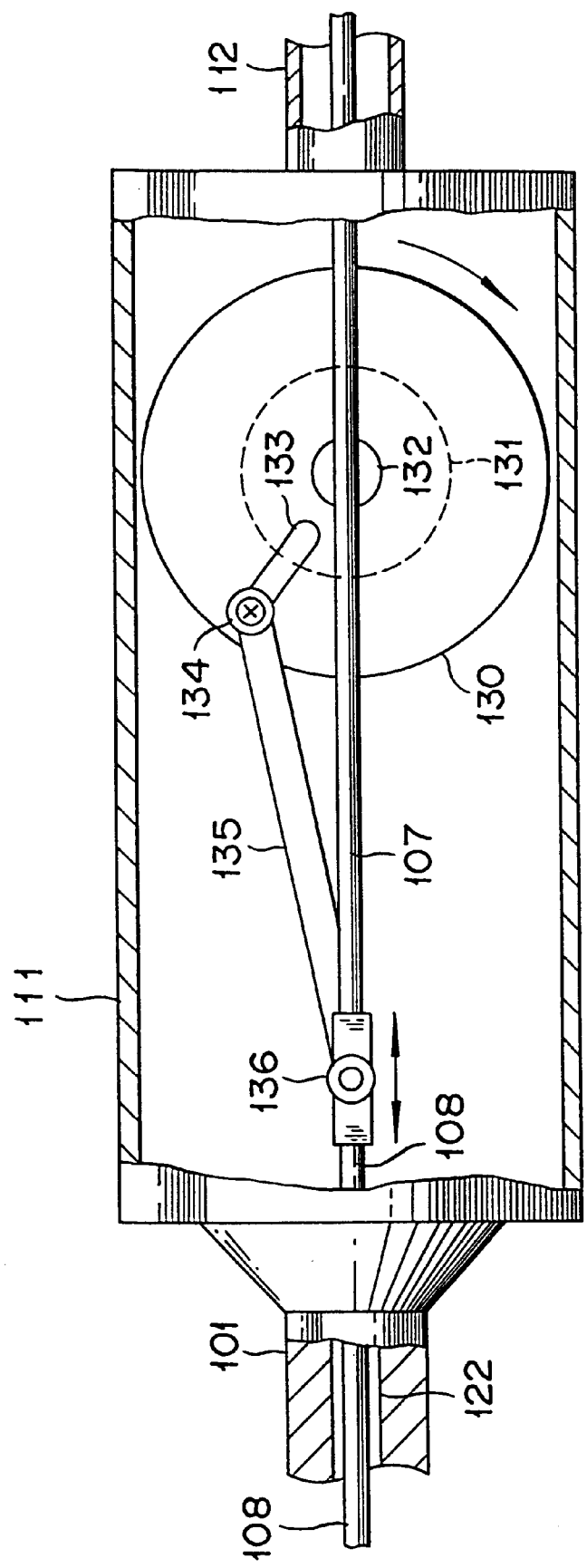
FIG. 6 is a partially broken plan view of a cam box of the laser irradiation apparatus.
Figure 7:
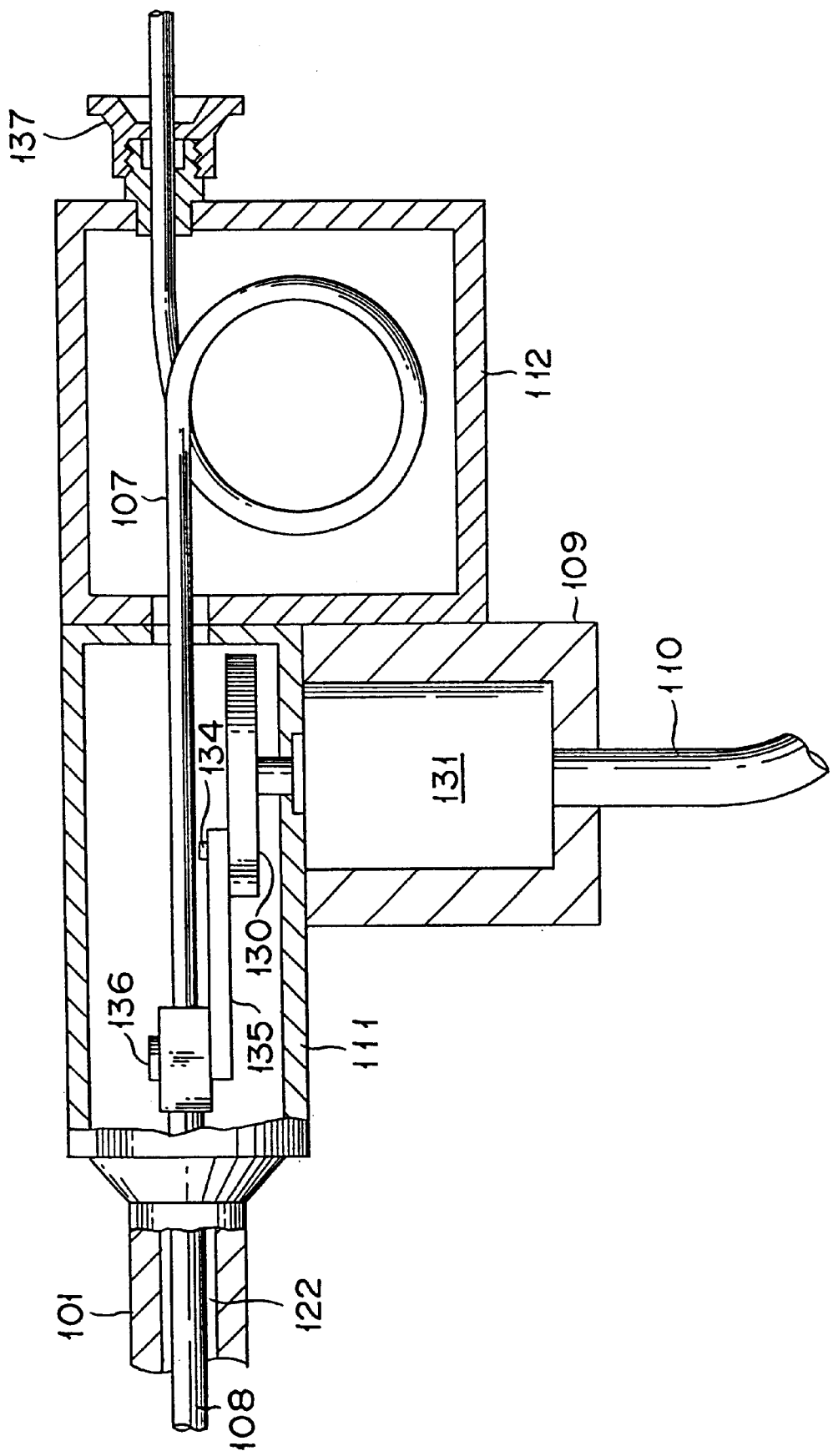
FIG. 7 is a partially broken side view showing the cam box, a drive unit and a buffer unit of the laser irradiation apparatus.

Next, let us describe the buffer unit 112, the cam box 111, and the drive unit 109 referring to FIG. 6 and FIG. 7.

The buffer unit 112 is provided to curb the excessive movement of optical fiber 107 outside of the apparatus 100. The buffer unit 112 comprises an opening for introducing the optical fiber 107 from the cam box 111, and a distal part 137 that has an opening to guide the optical fiber 107 to the outside of the apparatus 100. The optical fiber 107 is contained in loop-like condition in the buffer unit 112 and is affixed at the distal end 137. Therefore, the reciprocating motion of the optical fiber 107 is converted into a contraction and expansion motion inside the buffer unit 112. Thus, the optical fiber's motion and load are absorbed maintained internally, and the optical fiber does not move outside the apparatus 100.

The proximal end of the optical fiber 107 inside the main body 101 is covered by the protective pipe 108. The protective pipe 108 is held by the holding joint 136 inside the cam box 111 and the holding joint 136 transmits the reciprocating motion to the protective pipe 108.

A rotor 130 and a rod 135 are provided in the cam box 111. The rotor 130 has a shaft 132 connected to the shaft of the motor 131 of the drive unit 109 and a groove 133 formed in the radial direction on its surface. The rotor 130 is connected to one end of the rod 135 via a joint 134 that has a screw member. The joint 134 is located along the groove 133 and is fastened to the rotor 130 with the help of the screw member. The rod 135 is connected pivotally to the joint 134. Also, the other end of the rod 135 is pivotally connected to the holding joint 136 that holds the protective pipe 108. The range of reciprocation motion of the optical fiber 107 can be adjusted by changing the radius of rotation of the joint 134 by moving the fastening position of the joint 134. The protective pipe 108 ends at the proximal end of the holding joint 136.

The optical fiber 107, which is covered by the protective pipe 108 and is supported in such a way as to be able to slide freely inside the lumen 122 of the main body 101 as described above, is connected pivotally to the rod 135 via the holding joint 136 near the entrance of the lumen 122 inside the cam box 111, and extends into the buffer unit 112 through the cam box 111.

Furthermore, referring to FIG. 8A–FIG. 8D, the mechanism of the reciprocating motion of the optical fiber 107 is described. For the sake of explanation, some portions of the optical fiber 107 are simplified and not all details are shown.

The rotor 130 rotates around the shaft 132 driven by the motor 131. As a result, the optical fiber 107 performs a reciprocating motion in the axial direction of the main body 101 between the position shown in FIG. 8A and the position shown in FIG. 8C. Consequently, the range of the reciprocating motion of the distal end of the optical fiber 107 is twice the rotating radius R of the joint 134.

Figure 9:
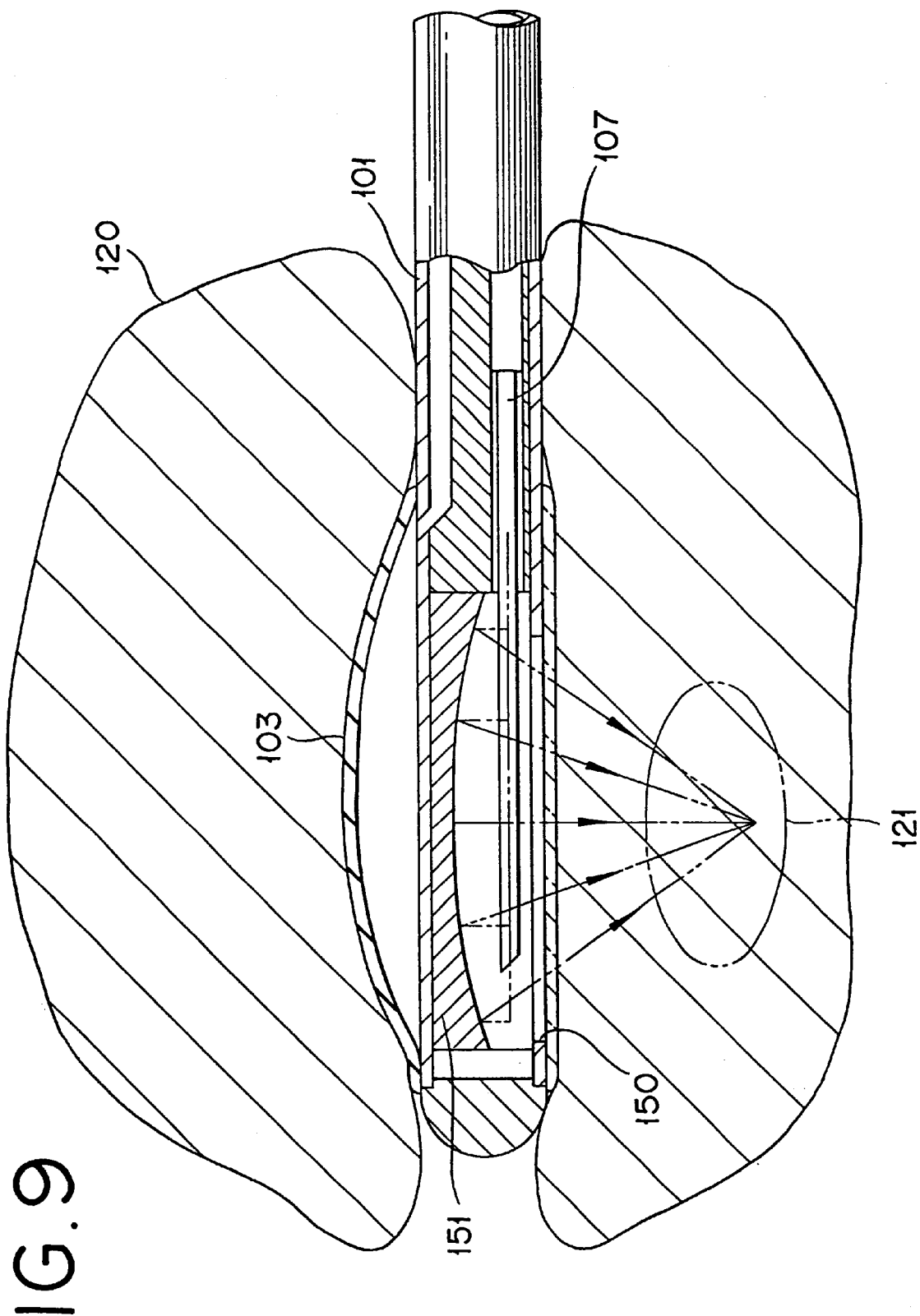
FIG. 9 is a drawing to describe how the laser irradiation apparatus according to the first embodiment of the invention is used.

Next, with reference to FIG. 9, let us describe the laser ray's passage when the distal end of the optical fiber 107 is at the distal side, middle, and proximal side positions of the main body 101.

As shown in FIG. 9, when the optical fiber 107 performs the reciprocating motion while emitting laser rays, the reflecting positions of the laser rays and the reflecting angles on the reflecting surface 152 constantly change and the laser rays passages converge on the target site 121. As the optical fiber 107 has a characteristic to pass the laser rays entering from the side, it does not present a big problem for the laser rays reflected by the reflecting surface 152 to be emitted through the window 150.

Next, let us describe how the laser irradiation apparatus 100 is used and its effect more specifically.

First, as shown in FIG. 9, the main body 101 is inserted led by its distal end into the urethra, and the distal end of the main body 101 is placed in the vicinity of the target site 121 of the prostate 120, which is the lesion in this case.

Next, the liquid for inflating the balloon is injected through the balloon inflating port 160 using a syringe, indeflator, etc. Thus, the balloon 103 is inflated to a specified size.

Next, turn on the cooling liquid circulating unit (not shown) to circulate the cooling liquid through the laser irradiation apparatus 100. The cooling liquid flows through the distal end space of the main body 101 via the cooling liquid inducing tube 105 and the lumen 122 and cools various parts of the main body 101 that are heated by the laser rays and the surface of the vital tissues contacting the cover 104.

Due to the expansion of the balloon 103, the window 150 side of the main body 101 where the balloon is not located is pressed against and makes a close contact with the surface of the urethra and is affixed there. Consequently, it is fixed in the direction of the target and the depth as the operator planned. Thus, the laser rays are securely irradiated against the target site of the vital tissue. Also, the area where the cover 104 is in contact or its vicinity, i.e., the surface layer of the vital tissue, is cooled by the cooling liquid so that the damage to the surface layer is securely prevented.

When the position of the distal end of the main body 101 becomes fixed, the motor 131 and then the laser generating unit are turned on. The laser ray generated by the laser generating unit is guided to the optical fiber 107 and emitted sideways at the distal end. The laser ray emitted from the distal end of the fiber 107 is reflected by the reflecting member 151 and emitted through the window 150 of the member 101 to be irradiated against the target site 121. Since the optical fiber 107 reciprocates at frequencies of 0.1–10 Hz, preferably 1–5 Hz, the light path of the laser ray changes continuously. The reflecting member 151 reflects the laser rays at such angles that the laser rays constantly cross or converge at the target site 121 regardless of the positions of the distal end of the optical fiber 107.

As a result, the target site 121 and its vicinity in the lesion 120 become heated by the irradiated laser rays and rise to the preferred temperature. On the other hand, the total irradiation quantity of the laser rays at an arbitrary point in the area above the target site 121 in FIG. 9, e.g., the surface layer of the lesion 120 is small, and the generated heat is also small. Similarly, the total irradiation quantity of the laser rays at an arbitrary point in the area below the target site 121 in FIG. 9, e.g., the area far from the main body 101 is small, and the generated heat is also small. In other words, the area in the vicinity of the target site 121 will not be affected much by the laser rays and be kept at relatively low temperatures. Since the damages of the areas other than the target site 121 are prevented or minimized, the apparatus 100 has a high treatment effect on the patient. It is particularly advantageous as the damage of the surface layer is prevented even when the target site 121 is located deep inside the vital tissue.

Next, the position of the target site 121 is changed within the lesion 120 and the laser rays are irradiated again. Repeating this process, multiple areas that need treatment that constitute the lesion 120 will be heated in turn.

The laser rays used in the apparatus 100 can be any type of rays as far as they have capabilities to reach deep inside the living body. However, the wavelengths of the laser rays are preferably 750–1300 nm or 1600 nm–1800 nm. This is so that the laser rays have excellent capabilities to reach deep inside the living body and are not absorbable in the surface layer of the living body. In other words, the laser rays in those wavelength ranges are more effectively applicable to the target site of the lesion existing deep inside the tissue.

The laser generating units that can generate laser rays in those wavelength ranges include gas lasers such as He-Ne lasers, solid lasers such as Nd-YAG lasers, and semiconductor lasers such as GaAlAs lasers.

The materials for the reflecting member 151 can be polyolefin such as polyethylene and polypropylene, ethylene-vinyl acetate copolymer (EVA), polyvinyl chloride, polyester such as polyethylene terephthalate and polybutylene terephthalate, polyamide, polyurethane, polystyrene, polycarbonate, fluororesin, polymer alloy containing one of the above, or a combination of more than two of them.

The surface of the main body 101 and/or the balloon 103 can be coated with a lubricating material such as hydrophilic polymer materials, silicon, fluorocarbon resin, etc. Such a coating will reduce the surface frictions of the parts that are inserted into the body cavities and will be helpful in inserting the main body 101 smoothly into the body cavities. It is also possible to prepare a throwaway type sheath to cover the main body 101 and apply lubricating materials on the surface of the sheath. This will make it possible to avoid the problem of losing lubricity as a result of the lubricating material's peel off when the equipment is used repeatedly.

The hydrophillic polymer materials are preferably carboxymethyl cellulose, polysaccharide, polyvinyl alcohol, polyethylene oxide, sodium polyacrylate, methylvinyl ether-maleic anhydride copolymer, water-soluble polyamide, etc., of which methylvinyl ether-maleic anhydride copolymer is most preferable.

When using a laser irradiation apparatus equipped with a main body 101 and a balloon 103 coated with a hydrophilic polymer, the main body 101 and the balloon 103 are immersed in physiological saline. This will cause the surface layers of the main body 101 and the balloon 103 wetted and make them lubricating. Thus, the frictions of the main body 101 and the balloon 103 will be reduced to lighten the patient's burden, and improve the treatment effect. Consequently, the insertion and pulling out from the body cavities, movement and rotation within the body cavities of the main body 101 can be done more smoothly.

The cover 104 is preferably constituted of materials with excellent light transmissibility such as PET (polyethylene terephthalate), quartz glass, acryl, polystyrene, polycarbonate, polyethylene, polypropylene, vinylidene chloride, fluorocarbon resin, and polyester.

Figure 10:
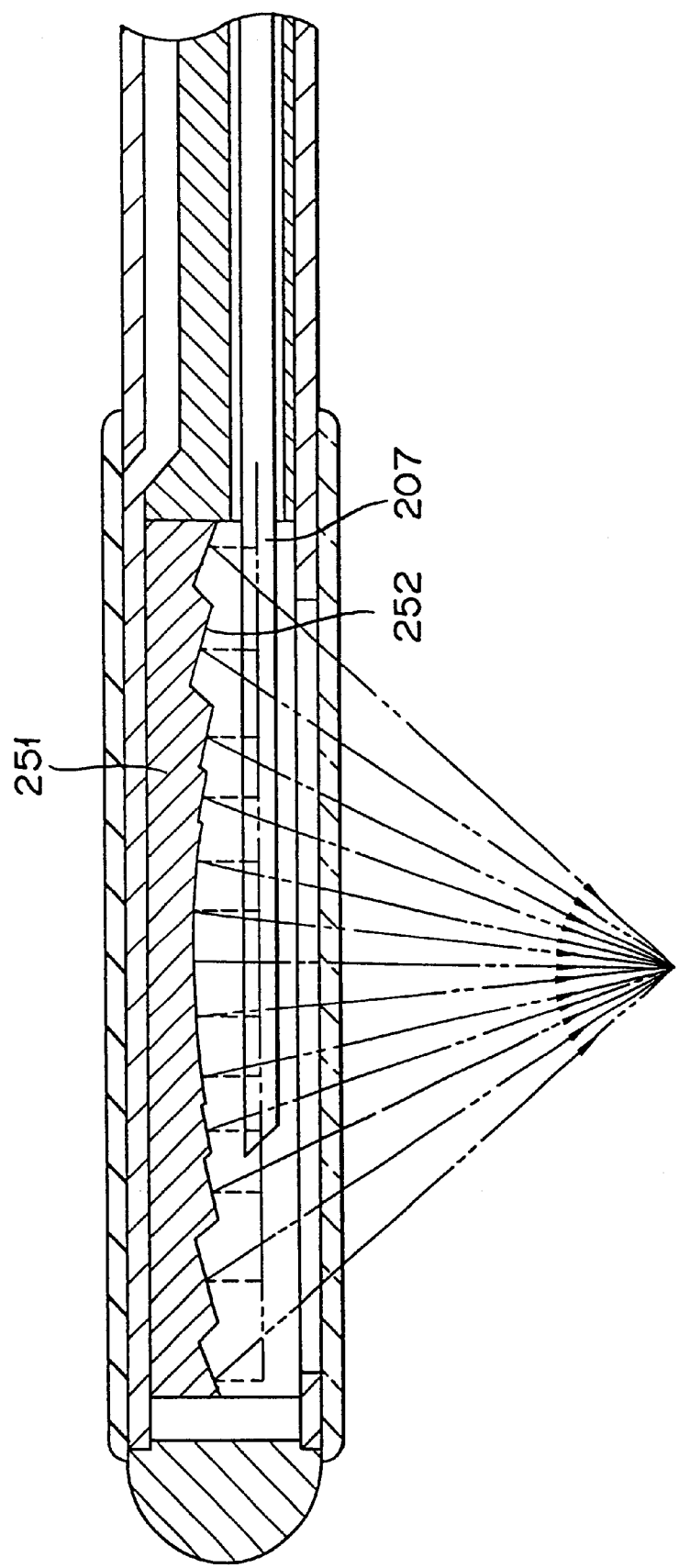
FIG. 10 is a drawing to describe the structure of the distal end of the main body of the laser irradiation apparatus according to the second embodiment.

Let us now describe the second embodiment of the invention referring to FIG. 10. The second embodiment differs from the first embodiment only in the structure of the reflecting member that reflects the laser rays. Therefore, only the differences from the first embodiment will be described in the following.

In FIG. 10, the reflecting member 251 has a reflecting surface 252 consisting of multiple small surfaces. The reflecting surface 252 is thus different from the reflecting surface 152 that consists of a continuous curved surface as in the case of the reflecting member 151 of the first embodiment. The multiple surfaces that constitute the reflecting surface 252 are formed in such angles that the laser rays from the optical fiber 207 will converge on a point as in the case of the continuous curved surface of the first embodiment. Moreover, the multiple surfaces are connected by stepped areas. This makes it possible to reduce the distance between the axis of the optical fiber 207 and the reflecting surface 252 even in the central area in the axial direction of the reflecting surface 252. This makes it possible to minimize the diameter of the main body 201. In order not to interfere with the laser ray passage, the stepped areas are provided with surfaces that are approximately parallel to the light path of the reflecting ray reflected by the reflecting surface 252 in the vicinities of the stepped areas. It is preferable not to have these stepped area surfaces be coated with reflecting films; it is preferable to have them coated with reflection preventive films in order to prevent irregular reflections.

The multiple surfaces that constitute the reflecting surface 252 can be flat surfaces if they are small enough. However, curved surfaces are preferable if they are relatively large surfaces.

Figure 11:
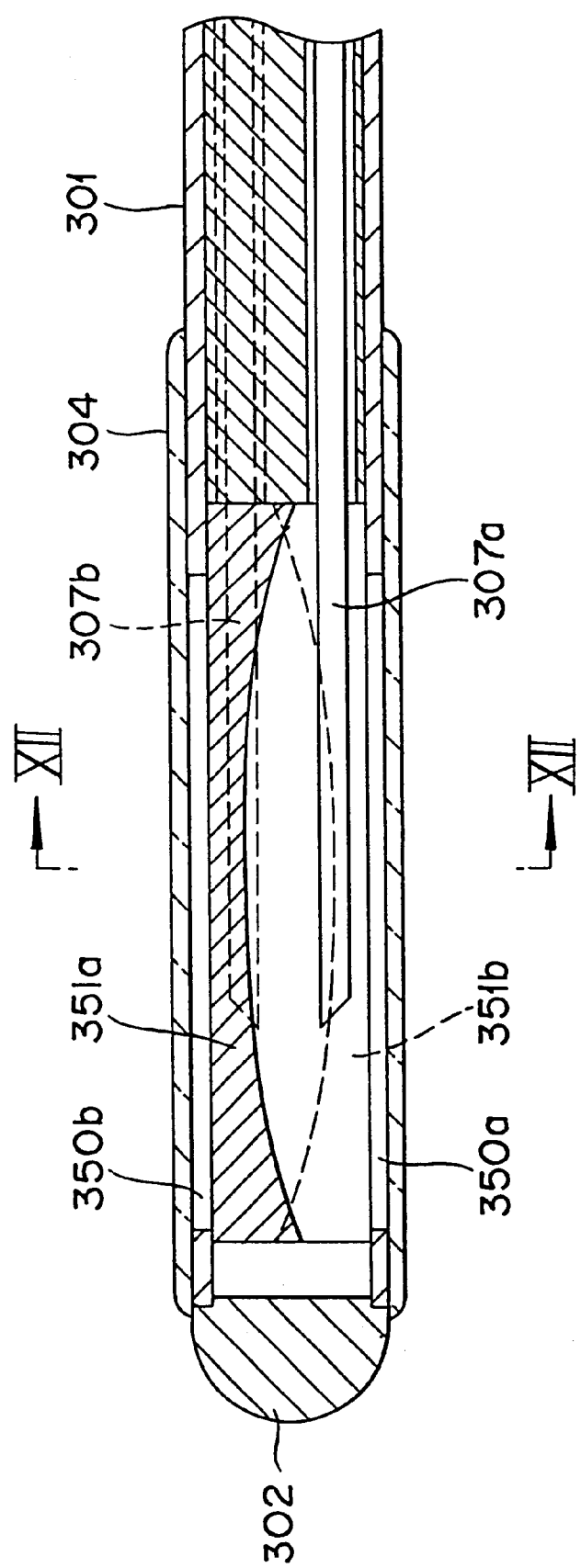
FIG. 11 is a drawing to describe the structure of the distal end of the main body of the laser irradiation apparatus according to the third embodiment.

Next, let us describe the third embodiment of the invention referring to FIG. 11. The third embodiment is characterized in that it uses two sets of the optical fiber and the reflecting member similar to those used in the first embodiment. Therefore, only the differences from the first embodiment will be described in the following.

FIG. 11 shows the positional relation schematically between the two optical fibers at the distal end of the laser irradiation apparatus according to the third embodiment of the invention.

As shown in FIG. 11, the distal end of the main body 301 of the laser irradiation apparatus of the third embodiment has two windows 350a and 350b for laser irradiation in up and down directions. No balloon is used in this arrangement and the cover 304 covers the entire circumference of the distal end of the main body 301.

Figure 12:
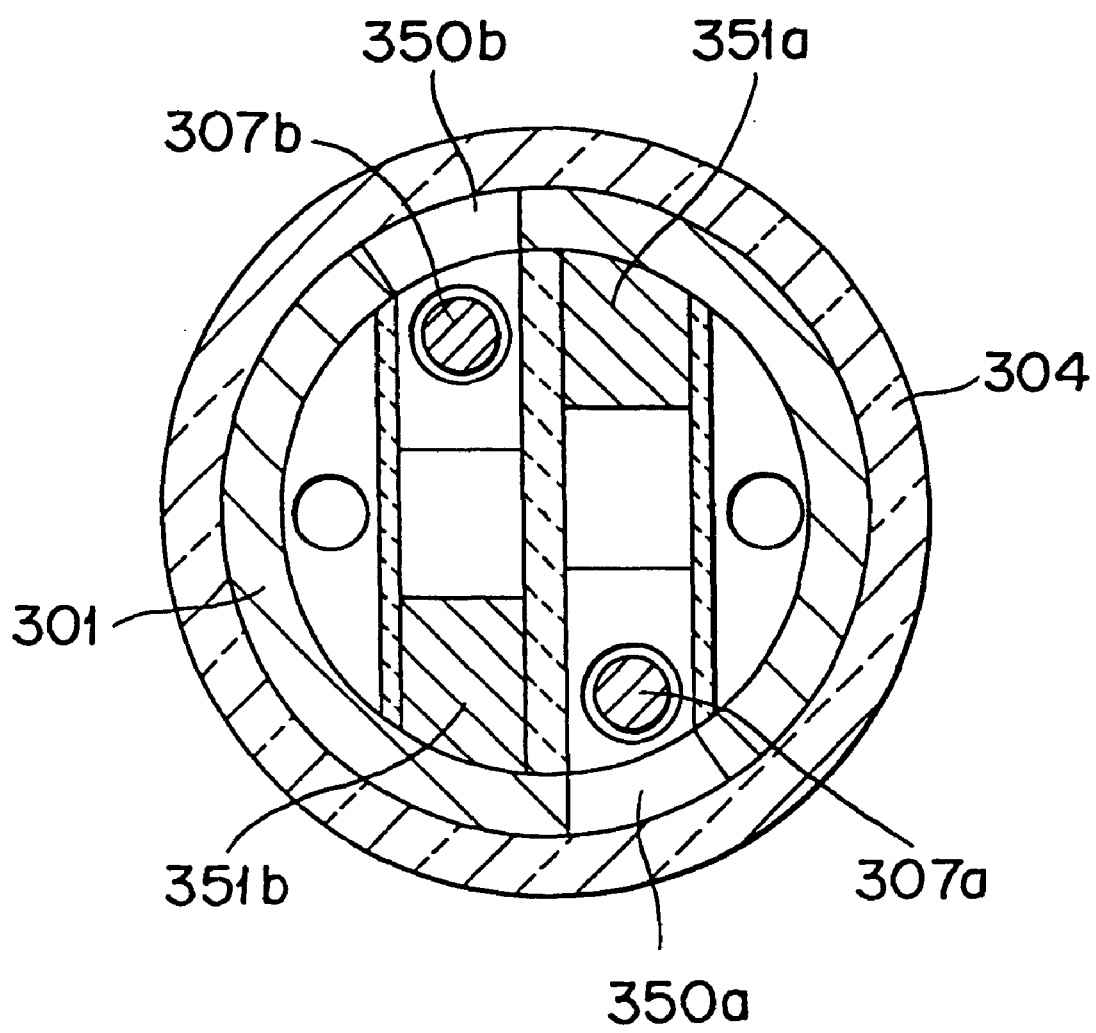
FIG. 12 is a cross sectional view taken along the line XII—XII of FIG. 11.

As can be seen from FIG. 12, two reflecting members 351a and 351b are arranged in a pair in the main body 301 in the third embodiment. The reflecting members 351a and 351b are constituted in a similar way as in the reflecting member 151 of the first embodiment. The reflecting members 351a and 351b are positioned in such a way that the direction of the reflecting surfaces are 180 degrees apart. The optical fibers 307a and 305b are also constituted in the similar manner as that of the first embodiment. The optical fibers 307a and 305b reciprocate within the spaced defined in the insides of the reflecting members 351a and 351b respectively.

The optical fibers 307a and 305b perform reciprocating motions through different lumens driven by the drive unit, which is connected to the distal end of the main body 301. The drive unit and the power transmission members are similar to those of the first embodiment shown in FIG. 7. In the third embodiment, the holding joint 136 shown in FIG. 7 holds two optical fibers together.

According to the third embodiment, laser rays can be emitted in two directions 180 degrees apart simultaneously. This makes it possible to treat the left and right sides of the prostate surrounding the urethra simultaneously and helps to minimize the operating time.

It is obvious that this invention is not limited to the particular embodiments shown and described above but may be variously changed and modified without departing from the technical concept of the invention.

This application is based on Japanese Patent Application No.11-305078 filed on Oct. 27, 1999, the contents of which are hereby incorporated by reference.

What is claimed is:

1. A laser irradiation apparatus comprising:
   a long and slender main body;
   a light conducting member, which is placed inside said main body and which is equipped with a proximal end through which a laser ray is introduced and an emitting part from which the laser ray is emitted sideways or diagonally, wherein said emitting part of said light conducting member is capable of reciprocating motion in the axial direction within a certain range; and
   a reflecting member, which is affixed to the inside of said main body to reflect the laser ray emitted from said light conducting member, wherein said reflecting member having a reflecting surface that changes its reflecting angle as said emitting part moves along its reciprocating movement range.

2. A laser irradiation apparatus of claim 1, wherein said reflecting angle of said reflecting surface is set at an angle to converge the laser rays emitted from said emitting part at a specified area while said emitting part reciprocates.

3. A laser irradiation apparatus of claim 1, wherein said reflecting surface has a parabolically curved surface.

4. A laser irradiation apparatus of claim 1, further comprising a drive unit that causes said light conducting member to perform a reciprocating motion.

5. A laser irradiation apparatus of claim 1, wherein multiple sets of said light conducting member and said reflecting member are provided.

6. A laser irradiation apparatus of claim 1, wherein said reflecting member is equipped with a pair of plate-like parts on both sides and the emitting part of said light conducting member is capable of reciprocating motion in a space defined by said pair of plate-like parts.

7. A laser irradiation apparatus of claim 6, wherein the inner surfaces of said pair of plate-like parts are coated with reflecting films that reflect laser rays.

8. A laser irradiation apparatus of claim 1, wherein said reflecting surface consists of a combination of multiple surfaces having angles varying along the lengthwise direction of said main body.

9. A laser irradiation apparatus of claims 8, wherein said multiple surfaces are connected by stepped areas formed between adjacent surfaces.

10. A laser irradiation apparatus of claim 9, wherein the surface of each of said multiple stepped areas is approximately parallel to the light path of the ray reflected by reflecting surfaces adjacent to said stepped area.

11. A laser irradiation apparatus of claim 10, wherein the surfaces of said stepped areas are coated with reflection preventive films.

* * * * *